(12) United States Patent
Wang et al.

(10) Patent No.: US 9,749,606 B2
(45) Date of Patent: Aug. 29, 2017

(54) BASELINE RESTORATION METHODS AND APPARATUSES AND MEDICAL DETECTING EQUIPMENTS THEREOF

(71) Applicant: SHENZHEN MINDRAY BIO-MEDICAL ELECTRONICS CO., LTD., Shenzhen (CN)

(72) Inventors: Pei Wang, Shenzhen (CN); Wenyu Ye, Shenzhen (CN); Shen Luo, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 197 days.

(21) Appl. No.: 14/822,582

(22) Filed: Aug. 10, 2015

(65) Prior Publication Data

US 2016/0344991 A1 Nov. 24, 2016

(30) Foreign Application Priority Data

May 22, 2015 (CN) .......................... 2015 1 0267251

(51) Int. Cl.
*H04B 1/10* (2006.01)
*H04N 9/68* (2006.01)
*G01T 1/17* (2006.01)

(52) U.S. Cl.
CPC ........... *H04N 9/68* (2013.01); *G01T 1/17* (2013.01)

(58) Field of Classification Search
CPC ...................................... H04N 9/68; G01T 1/17
USPC ................................ 375/316, 317, 346, 350
See application file for complete search history.

(56) References Cited

U.S. PATENT DOCUMENTS

2006/0093028 A1* 5/2006 Balan ................ H04L 25/03343
375/233
2007/0201544 A1* 8/2007 Zhu .................... H04L 25/03057
375/229

* cited by examiner

*Primary Examiner* — Siu Lee
(74) *Attorney, Agent, or Firm* — Kory D. Christensen; Polsinelli LLP

(57) ABSTRACT

This disclosure relates to baseline restoration methods and apparatuses and medical detecting equipment thereof. The baseline restoration method comprises: determining whether there is a high-amplitude baseline in an input signal by previous k output signals ($Y_1$, . . . , $Y_k$) of a filter, where k is a natural number and k≥1; setting the previous m output signals ($Y_1$, . . . , $Y_m$) of the filter as Y' when there is a high-amplitude baseline in the input signal, where Y' is a desired output signal of the filter; and using a current input signal $X_0$, the previous n input signals ($X_1$, . . . , $X_n$), and the previous m output signals ($Y_1$, . . . , $Y_m$) of said filter to obtain a current output signal $Y_0$ of said filter.

11 Claims, 2 Drawing Sheets

US 9,749,606 B2

BASELINE RESTORATION METHODS AND APPARATUSES AND MEDICAL DETECTING EQUIPMENTS THEREOF

TECHNICAL FIELD

This disclosure relates generally to medical electronics, particularly to baseline restoration methods and apparatuses and medical detecting equipment thereof.

BACKGROUND

Due to polarization voltage, zero drift and other factors, a baseline of a signal acquired would exceed a dynamic range of the signal during signal collection. When displayed, the signal with a high-amplitude baseline might not be displayed within a display area, or only part of the signal could be displayed within the display area.

In order to observe the complete signal, the baseline should be restored. Because the baseline is a low-frequency signal, a baseline restoration method provided by prior art uses a high-pass filter to remove the baseline. The frequency of the baseline is generally low, so the cut-off frequency of the high-pass filter should be very low. However, the lower the cut-off frequency of the high-pass filter, the longer the time required for the baseline to restore to zero, which leads to the baseline spending a very long time to restore to zero and the requirement for use could not be met. As shown in FIG. 1, assuming that the amplitude of the baseline is 1, the time required for the baseline to restore to zero by a high-pass filter would be more than 20 seconds.

SUMMARY

Disclosed here are embodiments of baseline restoration methods and apparatuses and medical detecting equipment thereof.

In one aspect, a baseline restoration apparatus comprises a filter, a high-amplitude baseline detector and a baseline restoration module.

The high-amplitude baseline detector detects whether there is a high-amplitude baseline in an input signal by the previous k output signals $(Y_1, \ldots, Y_k)$ of said filter, where k is a natural number and k≥1.

Said baseline restoration module sets previous m output signals $(Y_1, \ldots, Y_m)$ of said filter as Y' when there is a high-amplitude baseline in the input signal, where Y' is a desired output signal of said filter.

Said filter uses a current input signal $X_0$, the previous n input signals $(X_1, \ldots, X_n)$, and the previous m output signals $(Y_1, \ldots, Y_m)$ to obtain a current output signal $Y_0$ of said filter.

In another aspect, a baseline restoration method comprises:

determining whether there is a high-amplitude baseline in an input signal by the previous k output signals $(Y_1, \ldots, Y_k)$ of the filter, where k is a natural number and k≥1;

setting the previous m output signals $(Y_1, \ldots, Y_m)$ of the filter as Y' when there is a high-amplitude baseline in the input signal, wherein Y' is a desired output signal of the filter; and using a current input signal $X_0$, the previous n input signals $(X_1, \ldots, X_n)$, and the previous m output signals $(Y_1, \ldots, Y_m)$ of said filter to obtain a current output signal $Y_0$ of said filter.

In another aspect, a medical detecting equipment comprises a baseline restoration apparatus described above.

DETAILED DESCRIPTION

Figure 1:
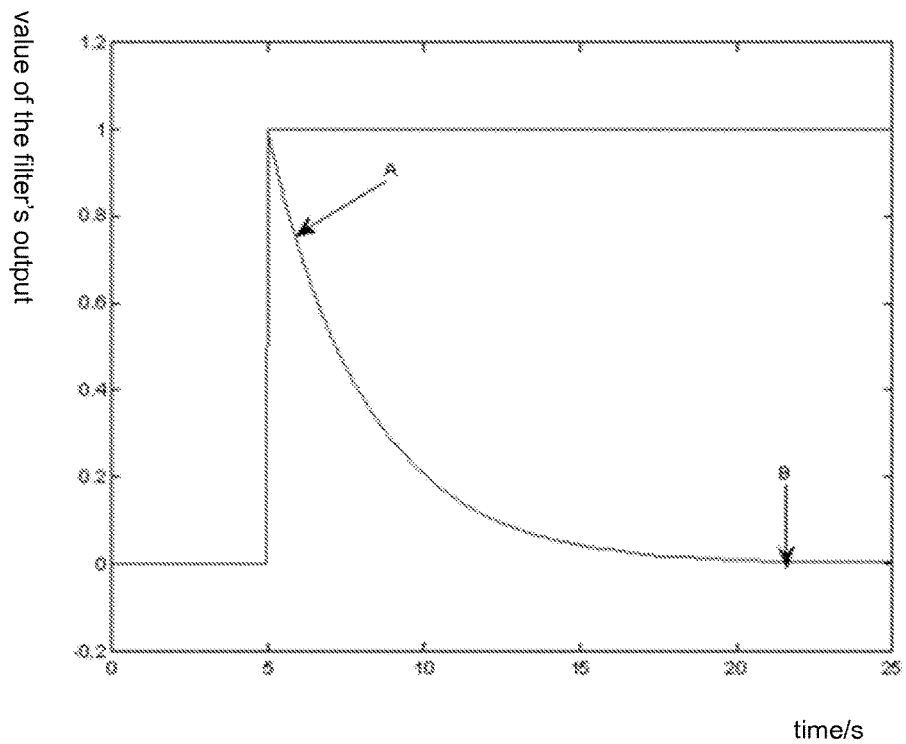
FIG. 1 shows an output signal of a high-pass filter used for baseline restoration in a prior art.
Figure 2:
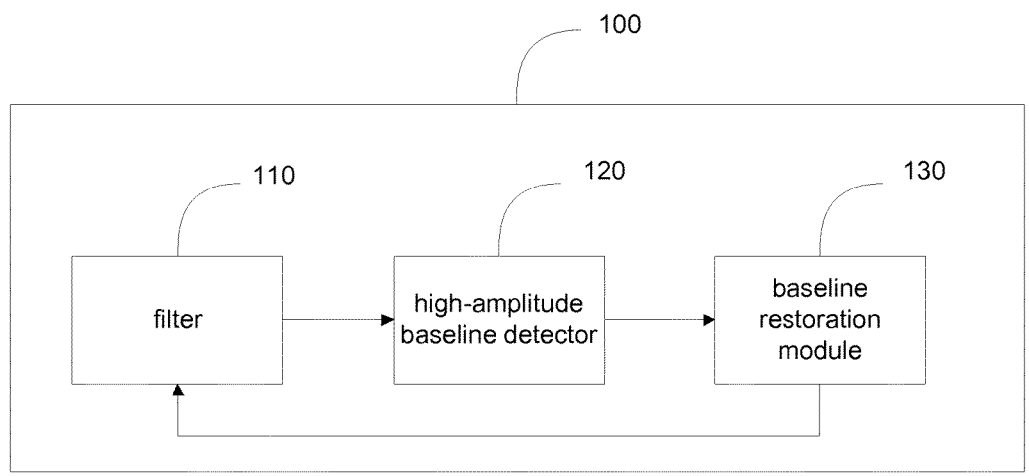
FIG. 2 shows a schematic diagram of a baseline restoration apparatus according to an embodiment.

As shown in FIG. 2, in one embodiment, a baseline restoration apparatus 100 comprises a filter 110, a high-amplitude baseline detector 120 and a baseline restoration module 130. An output port of the filter 110 may be connected to the high-amplitude baseline detector 120, the high-amplitude baseline detector 120 may be connected to the baseline restoration module 130, and the baseline restoration module 130 may be connected to the filter 110.

The high-amplitude baseline detector 120 may detect whether there is a high-amplitude baseline in an input signal by previous k output signals $(Y_1, \ldots, Y_k)$ of the filter, where k is a natural number and k≥1.

When the high-amplitude baseline detector 120 determines there is a high-amplitude baseline in the input signal, the previous m output signals $(Y_1, \ldots, Y_m)$ of the filter may be set to equal to Y' respectively by the baseline restoration module 130, that is, making $Y_1=Y', Y_2=Y', \ldots, Y_m=Y'$, where Y' is a desired output signal of the filter 110. When the high-amplitude baseline detector 120 determines there is no high-amplitude baseline in the input signal, the baseline restoration 130 does not do anything.

The filter 110 may use a current input signal $X_0$, the previous n input signals $(X_1, \ldots, X_n)$, and the previous m output signals $(Y_1, \ldots, Y_m)$ of the filter to obtain a current output $Y_0$ of the filter.

In this embodiment, when the high-amplitude baseline is detected, the previous m outputs $(Y_1, \ldots, Y_m)$ of the filter may be set to equal to the desired output signal Y' respectively. Thus the intermediate process, in which the output signal of the filter drops from the current output signal to the desired output signal, could be skipped, and the time required for the baseline to restore to zero could be decreased. In the meantime, the baseline restoration apparatus has nothing to do with the cut-off frequency of the filter, so it could guarantee that the filter band would not be distorted.

Figure 3:
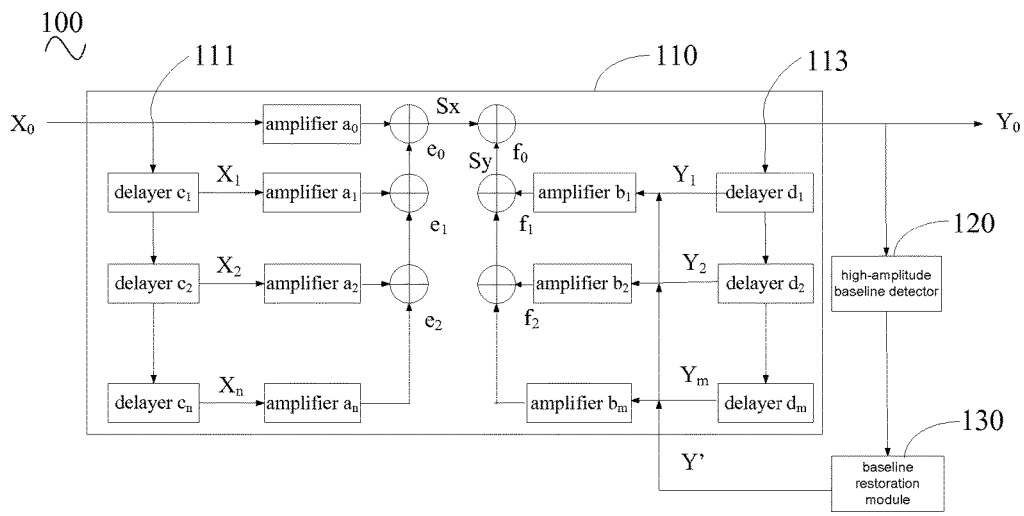
FIG. 3 shows a specific schematic diagram of the baseline restoration apparatus shown in FIG. 2.

FIG. 3 shows the specific schematic diagram of the baseline restoration apparatus shown in FIG. 2. In this embodiment, the filter 110 may be a high-pass filter, and the cut-off frequency of the filter 110 may be relatively low.

The filter 110 may comprise an input magnification part and an output magnification part. The input magnification part may comprise an input magnification branch and n input delay and magnification branches, and the output magnification branch may comprise an output branch and m output magnification branches.

For the input magnification part, in the input magnification branch, an input end 111 may be connected to an input end of an amplifier $a_0$, and an output end of the amplifier $a_0$ may be connected to a first input end of an adder $e_0$; in the first input delay and magnification branch, the input end 111 may be connected to an input end of a delayer $c_1$, a first output end of the delayer $c_1$ may be connected to an input end of an amplifier $a_1$, an output end of the amplifier $a_1$ may be connected to a first input end of an adder $e_1$, and an output end of the adder $e_1$ may be connected to a second input end of the adder $e_0$. In the second input delay and magnification branch, a second output end of the delayer $c_1$ may be connected to an input end of a delayer $c_2$, a first output end of the delayer $c_2$ may be connected to an input end of an adder $a_2$, an output end of the amplifier $a_2$ may be connected to a first input end of an adder $e_2$, and an output end of the adder $e_2$ may be connected to a second input end of the adder $e_1$; in turn, in the nth input delay and magnification branch, a second output end of a delayer $c_{n-1}$ may be connected to an input end of a delayer $c_n$, an output end of the delayer $c_n$ may be connected to an input end of an adder $a_n$, and an output end of the amplifier $a_n$ may be connected to a second input end of the adder $e_{n-1}$.

The input magnification part may be connected to the output magnification part by connecting an output end of the adder $e_0$ to a first input end of an adder $f_0$.

For the output magnification part, in the output branch, an output end 113 may be connected to the output end of the adder $f_0$; in the first output magnification branch, the output end 113 may be connected to an input end of a delayer $d_1$, a first output end of the delayer $d_1$ may be connected to an input end of an amplifier $b_1$, an output end of the amplifier $b_1$ may be connected to a first input end of an adder $f_1$, and an output end of the adder $f_1$ may be connected to the second input end of the adder $f_0$. In the second output magnification branch, the second output end of the delayer $d_1$ may be connected to an input end of a delayer $d_2$, the first input end of the delayer $d_2$ may be connected to the input end of an amplifier $b_2$, the output end of the amplifier $b_2$ may be connected to the first input end of an adder $f_2$, and the output end of the adder $f_2$ may be connected to the second input end of the adder $f_1$. In the mth output magnification branch, the second output end of a delayer $d_{m-1}$ may be connected to the input end of a delayer $d_m$, the output signal of the delayer $d_m$ may be connected to the input end of an amplifier $b_m$, and the output end of the amplifier $b_m$ may be connected to the second input end of the adder $b_{m-1}$.

In the first embodiment, the high-amplitude detector 120 may detect whether all the previous k output signals $(Y_1, \ldots, Y_k)$ of the filter are greater than a high-amplitude threshold. When all the previous k output signals $(Y_1, \ldots, Y_k)$ of the filter are greater than the high-amplitude threshold, the high-amplitude detector 120 may determine there is a high-amplitude baseline in the input signal. When not all the previous k output signals $(Y_1, \ldots, Y_k)$ of the filter are greater than the high-amplitude threshold, the high-amplitude detector 120 may determine there is no high-amplitude baseline in the input signal.

It could be understood that the high-amplitude threshold may be related to the input signal of the filter 110. The greater the amplitude of the input signal is, the greater the high-amplitude threshold may be; the less the amplitude of the input signal is, the less the high-amplitude threshold may be.

In the second embodiment, the high-amplitude detector 120 may detect whether the output energy of the filter 110 calculated using the previous k output signals $(Y_1, \ldots, Y_k)$ of the filter is greater than an energy threshold. When the output energy of the filter 110 is greater than the energy threshold, the high-amplitude detector 120 may determine there is a high-amplitude baseline in the input signal. When the output energy of the filter 110 is less than or equal to the energy threshold, the high-amplitude detector 120 may determine there is no high-amplitude baseline in the input signal.

It could be understood that the energy threshold may be related to the amplitude of the input signal of the filter 110. The greater the amplitude of the input signal is, the greater the energy threshold may be; the less the amplitude of the input signal is, the less the energy threshold may be.

When the high-amplitude baseline detector 120 determines there is a high-amplitude baseline in the input signal, the previous m output signals 110 $(Y_1, \ldots, Y_m)$ of the filter may be set as Y' respectively by the baseline restoration module 130, that is, making $Y_1$=Y', $Y_2$=Y', ..., $Y_m$=Y', where Y' is the desired output signal of the filter 110.

The filter 110 may use the current input signal $X_0$, the previous n input signals $(X_1, \ldots, X_n)$, and the previous m output signals $(Y_1, \ldots, Y_m)$ of the filter 110 to obtain the current output signal $Y_0$ of the filter.

For the input magnification part, the current input signal $X_0$ may be input into the amplifier $a_0$ and the delayer $c_1$ of the first input delay and magnification branch through the input end 111. The input signal $X_1$ stored in the delayer $c_1$ may be inputted into the amplifier $a_1$ to obtain the magnified signal $a_1X_1$, .... The value of the input signal $X_n$ outputted by the delayer $c_n$ of the nth input delay and magnification branch may be inputted into the amplifier $a_n$ to obtain an amplified signal $a_nX_n$.

The amplified signal $a_nX_n$ and $a_{n-1}X_{n-1}$ may be inputted into and summed by the adder $e_{n-1}$, and the output signal of the adder $e_{n-1}$ and the amplified signal $a_{n-2}X_{n-2}$ may be inputted into and summed by the adder $e_{n-2}$, .... In turn, the output signal of the adder $e_1$ and the amplified signal $a_0X_0$ may be inputted into and summed by the adder $e_0$, and the output signal of the adder $e_0$ may be the first sum value $S_x = a_0X_0 + a_1X_1 + \ldots + a_nX_n$.

For the output magnification part, the current output signal $Y_0$ may be inputted into the delayer $d_1$ of the first output magnification branch, the output signal $Y_1$ of the delayer $d_1$ may be inputted into the amplifier $b_1$ to obtain the magnified output signal $b_1Y_1$, and the output signal $Y_1$ may be inputted into the delayer $d_2$ of the second output magnification branch. The output signal $Y_{m-1}$ may be inputted into the delayer $d_m$ of the mth delay and magnification branch, and the output signal $Y_m$ stored in the delayer $d_m$ may be inputted into the magnification $b_m$ to obtain the magnified output signal $b_mY_m$.

The amplified output signal $b_mY_m$ and $b_{m-1}Y_{m-1}$ may be inputted into and summed by the adder $f_{m-1}$, the output signal of the adder $f_{m-1}$ and the magnified output signal $b_{m-2}Y_{m-2}$ may be inputted into and summed by the adder $f_{m-2}$, ..., and the output signal of the adder $f_2$ and the magnified output signal $b_1Y_1$ may be inputted into and summed by the adder $f_1$ to obtain the second sum value $S_y = b_1Y_1 + \ldots + b_mY_m$.

The first sum value $S_x$ outputted by the adder $e_0$ and the second sum value $S_y$ outputted by the adder $f_1$ may be inputted into and summed by the adder $f_0$ to obtain the current output signal $Y_0 = (a_0X_0 + a_1X_1 + \ldots + a_nX_n)(b_1Y_1 + \ldots + b_mY_m)$, where $Y_1$=Y', $Y_2$=Y', ..., $Y_m$=Y.

It could be understood that the structure of the filter 110 described above is just one embodiment of the present disclosure, and the filter 110 could be realized by other structures in other embodiments.

In addition, when the high-amplitude baseline detector 120 determines there is a high-amplitude baseline in the input signal, the baseline restoration module 130 may make $Y_1 = Y_1'$, $Y_2 = Y_2'$, ..., $Y_m = Y_m'$, where $Y_1'$, $Y_2'$, ..., and $Y_m'$ cannot be exactly the same. The output signal of the filter could decline rapidly when the difference among $Y_1', Y_2', \ldots,$ and $Y_m'$ is within a certain error range. The error range may be related to the amplitude of the input signal. The bigger the amplitude of the input signal, the bigger the error range allowed; the smaller the amplitude of the input signal, the smaller the error range allowed.

Figure 4:
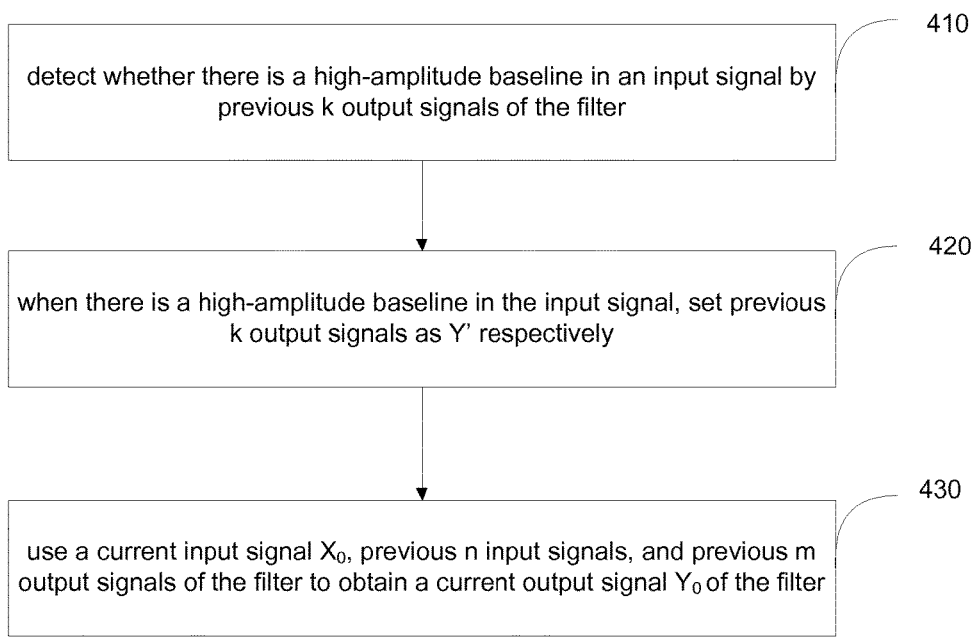
FIG. 4 shows a flow chart of a baseline restoration method according to one embodiment.

FIG. 4 shows a flow chart of a baseline restoration method in an embodiment. The baseline restoration method could include the following steps:

Step 410: detect whether there is a high-amplitude baseline in an input signal by previous k outputs $(Y_1, \ldots, Y_k)$ of the filter, where k is a natural number and k≥1. The filter could be a high-pass filter, and the cut-off frequency of the high-pass filter may be low.

Step 420: when there is a high-amplitude baseline in the input signal, set the previous m output signals $(Y_1, \ldots, Y_m)$ of the filter as Y' respectively, that is, making $Y_1=Y'$, $Y_2=Y', \ldots, Y_m=Y'$, where Y' is the desired output signal of the filter.

Step 430: use a current input signal $X_0$, previous n input signals $(X_1, \ldots, X_n)$, and previous m output signals $(Y_1, \ldots, Y_m)$ of the filter to obtain a current output $Y_0$ of the filter.

Step 410 could include the following steps: (1) detect whether all the previous k output signals $(Y_1, \ldots, Y_k)$ of the filter are greater than the high-amplitude threshold; (2) when all the previous k output signals of the filter are greater than the high-amplitude threshold, determine whether there is a high-amplitude baseline in the input signal; (3) when not all the previous k output signals of the filter are greater than the high-amplitude threshold, determine whether there is no high-amplitude baseline in the input signal.

In another embodiment, step 410 could include detecting whether the output energy of the filter calculated using the previous k output signals $(Y_1, \ldots, Y_k)$ of the filter is greater than an energy threshold. When the output energy of the filter is greater than the energy threshold, there is a high-amplitude baseline in the input signal; when the output energy of the filter is less than or equal to the energy threshold, there is not a high-amplitude baseline in the input signal.

Step 430 could include the following steps: (1) magnify the current input signal $X_0$ and the previous n input signals $(X_1, X_n)$ by magnification factors $(a_0, a_1, \ldots, a_n)$ respectively, (2) sum all magnified input signals to obtain a first sum value $S_x$, where n is a natural number and n≥1; (3) magnify the previous m output signals $(Y_1, \ldots, Y_m)$ of the filter by magnification factors $(b_1, \ldots, b_m)$ respectively, (4) sum all magnified output signals to obtain a second sum value $S_y$, where m is a natural number and m≥1; and (5) sum the first sum value $S_x$ and the second sum value $S_y$ to obtain a current output signal $Y_0=(a_0X_0+a_1X_1+ \ldots +a_nX_n)+(b_1Y_1+ \ldots +b_mY_m)$.

In this embodiment, the filter could be a high-pass filter.

This embodiment may be similar to the previous embodiments, the details of which could be understood to refer to FIGS. 2 and 3 and the related description above.

In one embodiment, a medical detecting equipment could comprise a baseline restoration apparatus described above, the details of which could be understood to refer to FIGS. 2 and 3 and the related description above.

In the above embodiments, when a high-amplitude baseline is detected, the previous m output signals $(Y_1, \ldots, Y_m)$ of the filter are set as Y' respectively. Thus the intermediate process in which the value of the filter's output drops from the current output signal to the desired output signal could be skipped, and the time required for the baseline to restore to zero could be decreased. In the meantime, the baseline restoration apparatus has nothing to do with the cut-off frequency of the filter, so it could guarantee that the filter band would not be distorted.

This disclosure has been made with reference to various exemplary embodiments. However, those skilled in the art will recognize that changes and modifications may be made to the exemplary embodiments without departing from the scope of the present disclosure. While the principles of this disclosure have been shown in various embodiments, many modifications of structure, arrangements, proportions, elements, materials, and components may be adapted for a specific environment and/or operating requirements without departing from the principles and scope of this disclosure. These and other changes or modifications are intended to be included within the scope of the present disclosure.

One of ordinary skill in the art will appreciate that all or parts of steps of the method could be executed by relative hardware under direction of a computer program, and the computer program could be stored in computer-readable storage media, which could be a magnetic disk, a light disk, a Read-Only Memory, a Random Access Memory, and so on.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. The scope of the present invention should, therefore, be determined by the following claims.

What is claimed is:

1. A baseline restoration apparatus, comprising:
a filter;
a high-amplitude baseline detector configured to detect whether there is a high-amplitude baseline in an input signal by previous k output signals $(Y_1, \ldots, Y_k)$ of said filter, wherein k is a natural number and k≥1; and
a baseline restorer configured to set previous m output signals $(Y_1, \ldots, Y_m)$ of said filter as Y' when there is a high-amplitude baseline in the input signal, wherein Y' is a desired output signal of said filter, wherein
said filter uses a current input signal $X_0$, the previous n input signals $(X_1, \ldots, X_n)$, and the previous m output signals $(Y_1, \ldots, Y_m)$ to obtain a current output signal $Y_0$ of said filter, wherein m and n are natural numbers, and m and n are greater than or equal to 1.

2. The baseline restoration apparatus of claim 1, wherein said high-amplitude detector determines there is a high-amplitude baseline in the input signal when the previous k output signals $(Y_1, \ldots, Y_k)$ of the filter are all greater than a high-amplitude threshold, and determines there is no high-amplitude baseline in the input signal when not all the previous k output signals $(Y_1, \ldots, Y_k)$ are greater than the high-amplitude threshold.

3. The baseline restoration apparatus of claim 1, wherein said high-amplitude detector determines there is a high-amplitude baseline in the input signal when an output energy of said filter calculated using the previous output signals $(Y_1, \ldots, Y_k)$ is greater than an energy threshold, and determines there is no high-amplitude baseline in the input signal when the output energy of said filter is less than or equal to the energy threshold.

4. The baseline restoration apparatus of claim 1, wherein said filter magnifies the current input signal $X_0$ and the previous n input signals $(X_1, \ldots, X_n)$ by magnification factors $(a_0, a_1, \ldots, a_n)$ respectively and sums the magnified input signals to obtain a first sum value $S_x$, magnifies the previous m output signals $(Y_1, \ldots, Y_m)$ by magnification factors $(b_1, \ldots, b_m)$ respectively and sums the magnified output signals to obtain a second sum value $S_y$, and adds the first sum value $S_x$ and the second sum value $S_y$ to obtain the current output signal of the filter $Y_0 = (a_0 X_0 + a_1 X_1 + \ldots + a_n X_n) + (b_1 Y_1 + \ldots + b_m Y_m)$, wherein n is a natural number and $n \geq 1$, and m is a natural number and $m \geq 1$.

5. The baseline restoration apparatus of claim 1, wherein said filter is a high-pass filter.

6. A medical detecting equipment, wherein said equipment comprises the baseline restoration apparatus of claim 1.

7. A baseline restoration method, comprising:
   determining that there is a high-amplitude baseline in an input signal by previous k output signals $(Y_1, \ldots, Y_k)$ of a filter, wherein k is a natural number and $k \geq 1$;
   setting previous m output signals $(Y_1, \ldots, Y_m)$ of said filter as Y' when there is a high-amplitude baseline in the input signal, wherein Y' is a desired output signal of the filter; and
   using a current input signal $X_0$, the previous n input signals $(X_1, \ldots, X_n)$, and the previous m output signals $(Y_1, \ldots, Y_m)$ of said filter to obtain a current output signal $Y_0$ of said filter, wherein m and n are natural numbers, and m and n are greater than or equal to 1.

8. The method of claim 7, wherein determining that there is a high-amplitude baseline in an input signal by previous k output signals $(Y_1, \ldots, Y_k)$ of said filter comprises:
   determining whether the previous k output signals $(Y_1, \ldots, Y_k)$ of said filter are all greater than a high-amplitude threshold; and
   determining whether there is a high-amplitude baseline in the input signal when all of the previous k outputs of said filter are greater than the high-amplitude threshold, and there is no high-amplitude baseline in the input signal when not all of the previous k output signals of said filter are greater than the high-amplitude threshold.

9. The method of claim 7, wherein determining whether there is a high-amplitude baseline in an input signal by the previous k output signals $(Y_1, \ldots, Y_k)$ of said filter comprises:
   determining whether an output energy of said filter calculated using the previous k output signal $(Y_1, \ldots, Y_k)$ of said filter is greater than an energy threshold; and
   determining whether there is a high-amplitude baseline in the input signal when the output energy of said filter is greater than the energy threshold, and there is no high-amplitude baseline in the input signal when the output energy of said filter is less than or equal to the energy threshold.

10. The method of claim 7, wherein using the current input signal $X_0$, the previous n input signals $(X_1, \ldots, X_n)$, and the previous m output signals $(Y_1, \ldots, Y_m)$ of said filter to obtain the current output signal $Y_0$ of said filter comprises:
    magnifying the current input signal $X_0$ and the previous n input signals $(X_1, \ldots, X_n)$ by magnification factors $(a_0, a_1, \ldots, a_n)$ respectively, wherein n is a natural number and $n \geq 1$;
    summing the magnified input signals to obtain a first sum value $S_x$;
    magnifying the previous m output signals $(Y_1, \ldots, Y_m)$ of said filter by magnification factors $(b_1, \ldots, b_m)$ respectively;
    summing the magnified output signals to obtain a second sum value $S_y$; and
    summing the first sum value $S_x$ and the second sum value $S_y$ to obtain the current output signal $Y_0 = (a_0 X_0 + a_1 X_1 + \ldots + a_n X_n) + (b_1 Y_1 + \ldots + b_m Y_m)$ of said filter, wherein m is a natural number and $m \geq 1$.

11. The method of claim 7, wherein said filter is a high-pass filter.

* * * * *